United States Patent
Bayer

[19]

[11] Patent Number: 6,126,594
[45] Date of Patent: Oct. 3, 2000

[54] ANOSCOPE FOR INTERNAL HEMORRHOIDECTOMY

[76] Inventor: Izhack Bayer, 58 Ahad Aam St., Herzelia, Israel

[21] Appl. No.: 09/119,400

[22] Filed: Jul. 21, 1998

[51] Int. Cl.[7] .................................................. A61B 1/00
[52] U.S. Cl. ............................................ 600/184; 600/190
[58] Field of Search .................................. 600/184, 200, 600/196, 190, 208; 606/197, 198

[56] References Cited

U.S. PATENT DOCUMENTS

| | | | |
|---|---|---|---|
| 52,014 | 1/1866 | Bartlet | 600/184 |
| 540,838 | 6/1895 | Gunning | 606/198 |
| 1,244,751 | 10/1917 | McCleary | 606/197 |
| 1,827,497 | 10/1931 | Varney | 606/198 |
| 2,184,642 | 12/1939 | Glass | 606/197 |
| 3,044,461 | 7/1962 | Murdock | 600/187 |
| 3,721,229 | 3/1973 | Panzer | 606/198 |
| 4,527,553 | 7/1985 | Upsher | 600/199 |
| 4,834,067 | 5/1989 | Block | 600/184 |
| 4,996,916 | 3/1991 | Nakagawa | 600/241 |
| 5,165,387 | 11/1992 | Woodson | 600/184 |
| 5,249,568 | 10/1993 | Brefka et al. | 600/184 |
| 5,404,870 | 4/1995 | Brinkerhoff et al. | 600/184 |
| 5,505,690 | 4/1996 | Patton et al. | 600/184 |
| 5,509,893 | 4/1996 | Pracas | 600/184 |
| 5,716,329 | 2/1998 | Dieter | 600/184 |
| 5,743,852 | 4/1998 | Johnson | 600/184 |

*Primary Examiner*—Paul J. Hirsch
*Attorney, Agent, or Firm*—Christopher E. Blank, Esq; Lynne M. Blank, Esq

[57] ABSTRACT

Hemorrhoidectomy apparatus comprising an anoscope comprising a generally cylindrical body having a longitudinal axis, said body comprising an open proximal portion and an open distal portion, said proximal portion comprising a generally cylindrical ring from which distally extend a plurality of strips annularly spaced from each other about the longitudinal axis of said body.

9 Claims, 5 Drawing Sheets

ANOSCOPE FOR INTERNAL HEMORRHOIDECTOMY

FIELD OF THE INVENTION

The present invention relates generally to an anoscope for internal hemorrhoidectomy and particularly for an anoscope for surgical stapling hemorrhoidectomy.

BACKGROUND OF THE INVENTION

Several methods for removing hemorrhoids are known in the art. Surgical stapling hemorrhoidectomy was introduced in the early 1990's on the basis of the so-called Whitehead closed technique for complete rectal-mucosal prolapse combined with hemorrhoids. Transection of piles through a circular stapler was first suggested by Prof. G. Allegra of the University of Florence in 1990. In 1995, Dr. J. J. O'Connor of Suburban Hospital, Bethesda, USA, and Dr. C. V. Devien of L'HOpital St. Cloud, Paris, France, performed a hemorrhoidectomy with a linear stapler.

In 1993, Dr. A. Longo of the University of Plaermo, Italy, introduced a new technique for circular stapler hemorrhoidectomy. The Longo technique involves removing internal hemorrhoids only above the dentate line. After local anesthesia, and preferably anal dilatation to avoid injury to the sphincters, a purse-string suture is made 2–3 cm above the dentate line, at the level of the origin of the internal hemorrhoids, including all internal piles, as seen in FIG. 1. The purse-string suture includes only mucosa, submucosa and hemorrhoidal tissue. In the event of large mucosal prolapse, another purse-string suture may be made above the first one. A circular stapler is inserted in the rectum beyond the purse-string sutures and the sutures are secured to the anvil shaft of the stapler, as seen in FIG. 2. The stapler is then closed and fired, thereby cutting the hemorrhoids and performing a muco-mucosal anastomosis, as seen in FIG. 3. Titanium staples are generally expelled within 3–40 days (see "Painless Haemorrhoidectomy and Mucous Prolapsectomy (PHP)", Ethicon Endo-Surgery, a Johnson & Johnson Company).

Anoscopes for performing hemorrhoidectomies are known. For example, U.S. Pat. No. 4,834,067 to Block, the disclosure of which is incorporated herein by reference, describes an instrument for internal hemorrhoidectomy. The described instrurment has a partial cylindrical body particularly useful for obliterative suturing. Although the instrument permits suturing a single hemorrhoid, nevertheless the instrument hinders suturing a plurality of hemorrhoids located about the inner perimeter of the rectal wall.

There is thus a need for an anoscope which permits suturing a plurality of hemorrhoids located about the inner perimeter of the rectal wall.

SUMMARY OF THE INVENTION

The present invention seeks to provide an improved anoscope which permits suturing a plurality of hemorrhoids located about the inner perimeter of the rectal wall. The anoscope of the present invention is suitable for performing obliterative suturing of hemorrhoids (i.e., strangulation of the hemorrhoids) as well as removal of the hemorrhoids by a circular stapler, particular by the Longo method. The anoscope provides convenient access to any number of hemorrhoids at any angle. Illuminating apparatus can be disposed through the anoscope if desired. The anoscope may be manufactured of any material, size or configuration, and can be disposable.

It is noted that throughout the specification and claims the terms anoscope and proctoscope are synonymous.

There is thus provided in accordance with a preferred embodiment of the present invention hemorrhoidectomy apparatus comprising an anoscope comprising a generally cylindrical body having a longitudinal axis, said body comprising an open proximal portion and an open distal portion, said proximal portion comprising a generally cylindrical ring from which distally extend a plurality of strips annularly spaced from each other about the longitudinal axis of said body.

In accordance with a preferred embodiment of the present invention said strips are generally parallel to the longitudinal axis.

Further in accordance with a preferred embodiment of the present invention said strips generally do not extend radially beyond said ring.

Still further in accordance with a preferred embodiment of the present invention said strips are spaced generally symmetrically about the longitudinal axis of said body.

Additionally in accordance with a preferred embodiment of the present invention a handle extends from said proximal portion.

In accordance with a preferred embodiment of the present invention a dilator is disposed through said body.

Further in accordance with a preferred embodiment of the present invention the dilator comprises a generally elongate cylindrical body with a generally rounded distal end disposed through said body.

Still further in accordance with a preferred embodiment of the present invention illumination apparatus is disposed through said body.

BRIEF DESCRIPTION OF THE DRAWINGS

The following description will best be understood in conjunction with the following drawings.

DETAILED DESCRIPTION OF A PREFERRED EMBODIMENT

Figure 1:
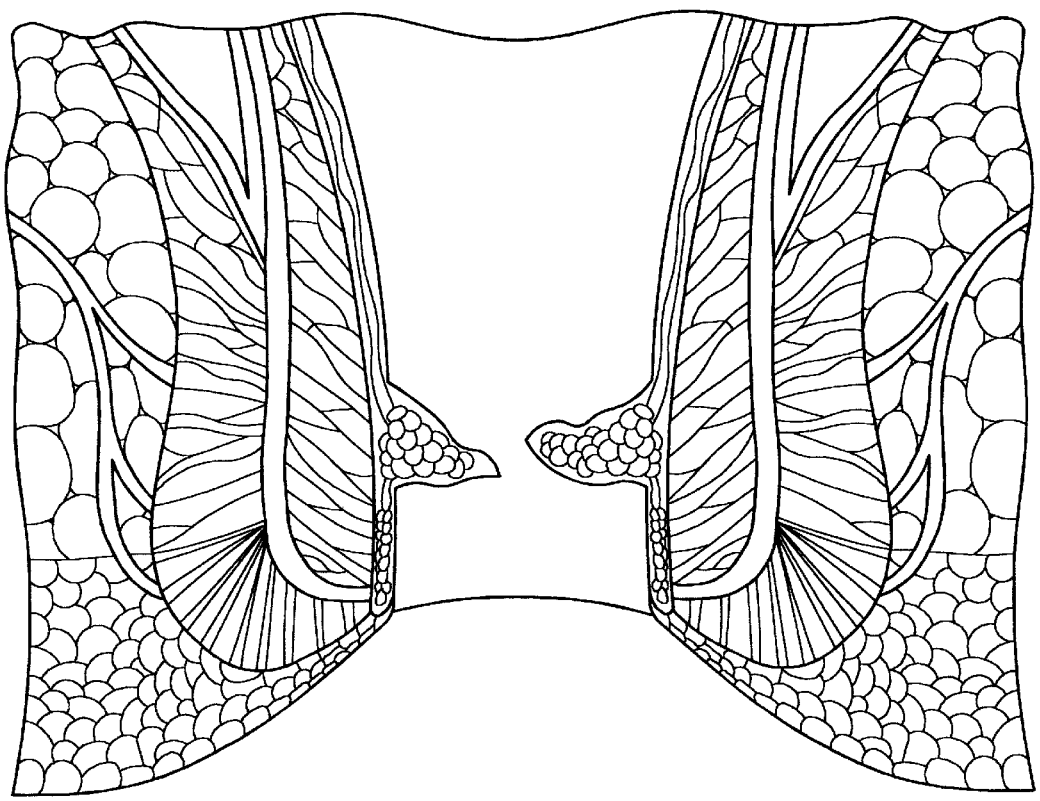
FIGS. 1, 2 and 3 are simplified illustrations of the prior art Longo method for circular stapler hemorrhoidectomy.
Figure 2:
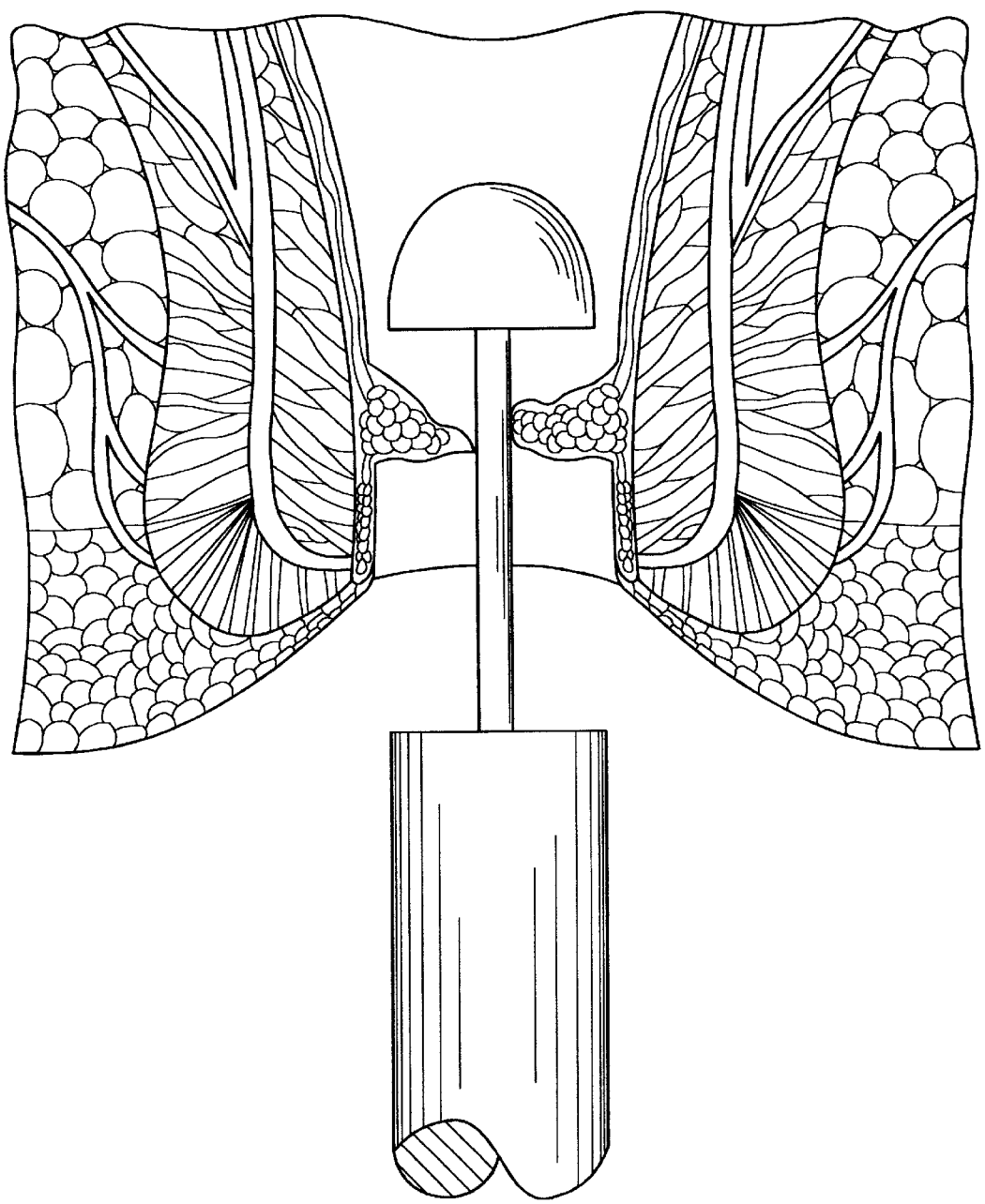
Figure 3:
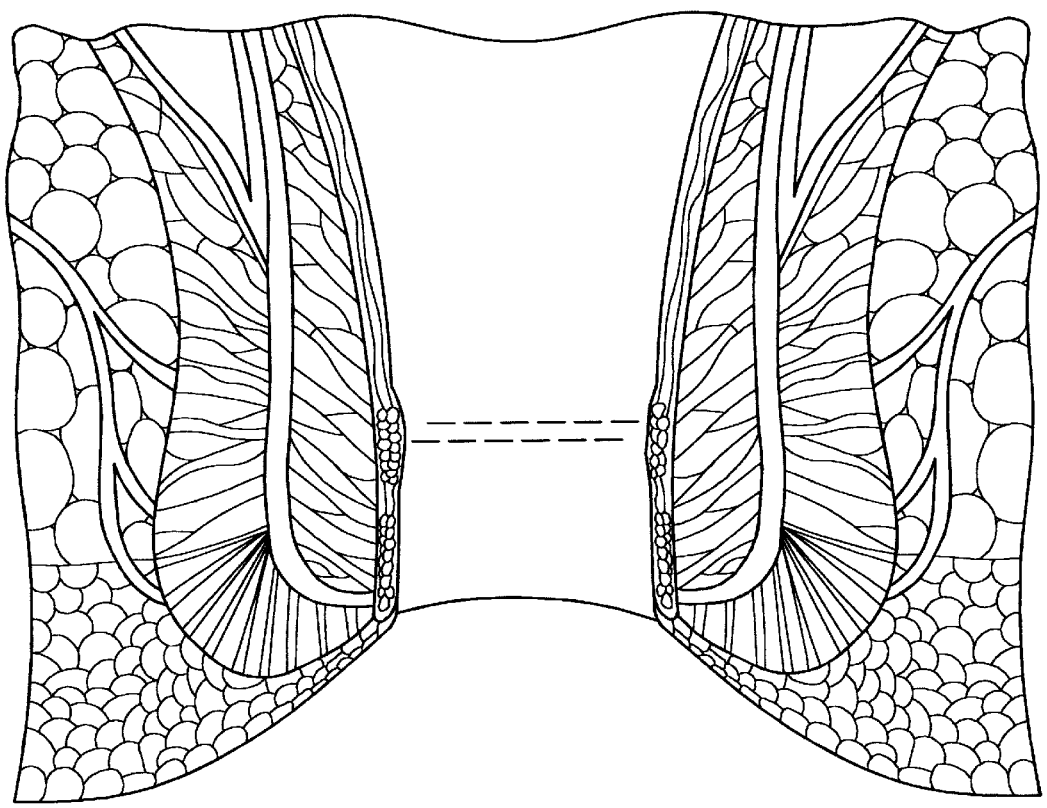
Figure 4:
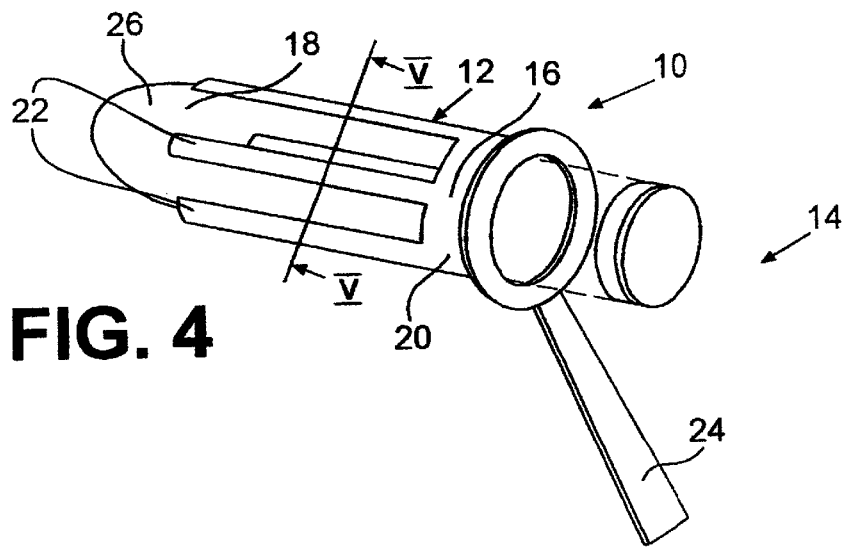
FIG. 4 is a simplified illustration of an anoscope constructed and operative provided in accordance with a preferred embodiment of the present invention.
Figure 5:
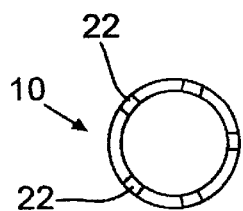
FIG. 5 is a simplified sectional illustration of the anoscope of FIG. 4, taken along lines V—V in FIG. 4.

Reference is now made to FIGS. 4 and 5 which illustrate an anoscope 10 constructed and operative provided in accordance with a preferred embodiment of the present invention. Anoscope 10 preferably includes a generally cylindrical body 12 having a longitudinal axis 14. Body 12 preferably includes an open proximal portion 16 and an open distal portion 18. Since distal portion 18 is open, anoscope 10 can be freely withdrawn from the rectum after suturing the hemorrhoids without interfering with the sutures.

Proximal portion 16 preferably includes a generally cylindrical ring 20 from which distally extend a plurality of strips 22 annularly spaced from each other about longitudinal axis 14. Strips 22 are generally parallel to longitudinal axis 14, and generally do not extend radially beyond ring 20. Most preferably strips 22 are spaced generally symmetrically about longitudinal axis 14. Alternatively, the spacing between strips 22 may be variable, if desired. A handle 24 preferably extends from proximal portion 16 away from axis 14.

Figure 6:
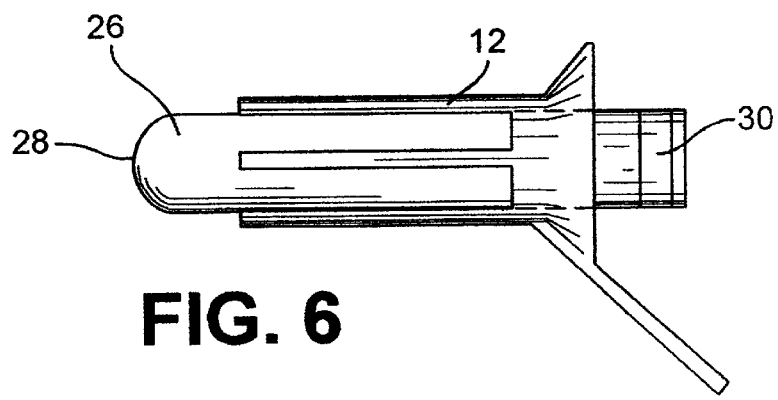
FIG. 6 is a simplified side-view illustration of the anoscope of FIG. 4, showing a dilator inserted in the anoscope.

Reference is now made to FIG. 6 which shows a dilator 26 disposed through body 12. Dilator 26 is preferably constructed of a low friction material, such as TEFLON. Dilator 26 preferably includes a generally elongate cylindrical body with a generally rounded distal end 28 disposed through body 12. Dilator 26 is initially placed inside and through anoscope 10 during insertion of anoscope 10 into the rectum of a patient. Dilator 26, and especially the rounded end 28, provide a comfortable structure for easy insertion into the anus and rectum. Dilator 26 preferably has a proximal gripping portion 30 for easy withdrawal of the dilator after insertion of anoscope 10 in the rectum.

Figure 7:
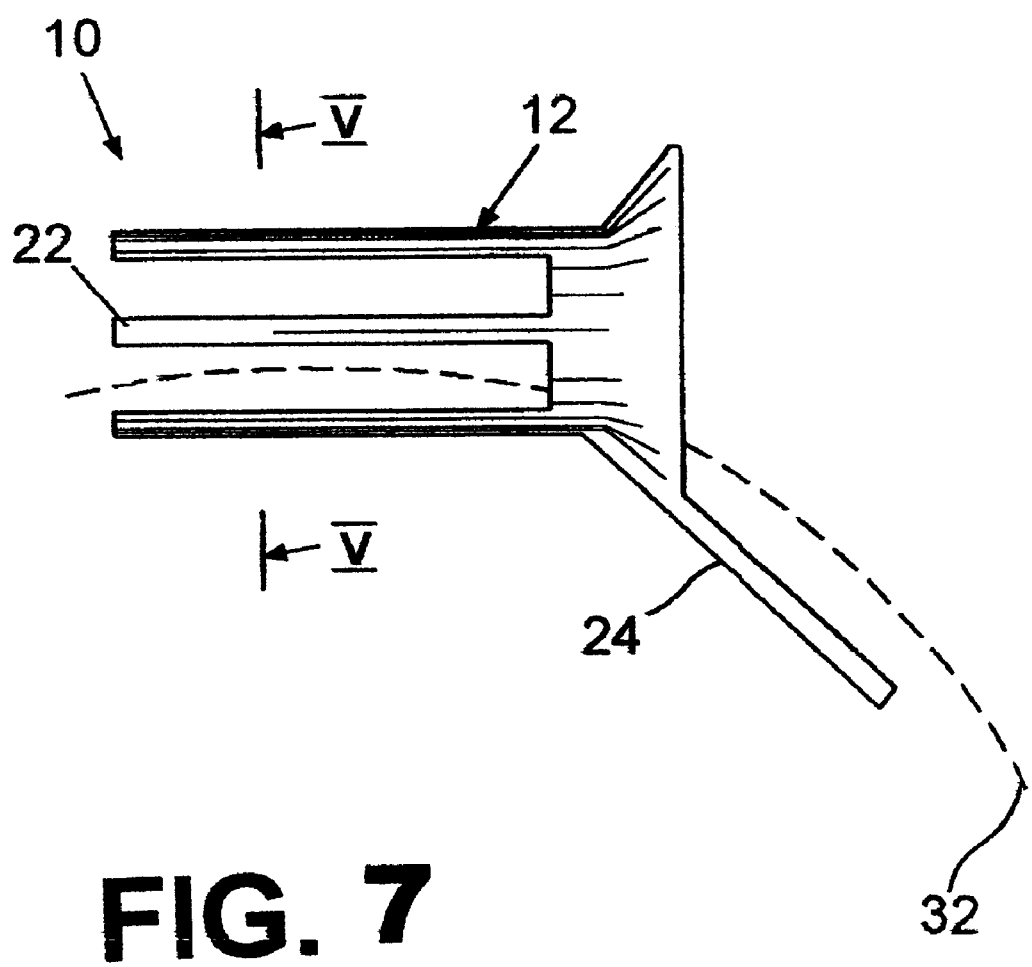
FIG. 7 is a simplified side-view illustration of the anoscope of FIG. 4, showing illuminating apparatus inserted in the anoscope.

Reference is now made to FIG. 7 which illumination apparatus 32 disposed through body 12. Illumination apparatus 32 can be built integrated in the anoscope walls and handle. Illumination apparatus 32 may be any kind of illumination apparatus, such as an optic fiber. It is appreciated that any kind of substance or instrument can be introduced through anoscope 10 into the rectum, if desired.

What is claimed is:

1. A hermorrhoidecomy apparatus comprising: an anoscope comprising a generally cylindrical body having a longitudinal axis, said body comprising an open proximal portion and an open distal portion, said proximal portion comprising a generally cylindrical ring from which distally extend a plurality of strips annularly spaced from each other about the longitudinal axis of said body.

2. The hemorrhoidecomy apparatus according to claim 1 and wherein said strips are generally parallel to the longitudinal axis.

3. The hemorrhoidecomy apparatus according to claim 1 and wherein said strips generally do not extend radially beyond said ring.

4. The hemorrhoidecomy apparatus according to claim 1 and wherein said strips are spaced generally symmetrically about the longitudinal axis of said body.

5. The hemorrhoidecomy apparatus according to claim 1 and comprising a handle extending from said proximal portion.

6. The hemorrhoidecomy apparatus according to claim 1 further comprising a dilator disposed through said body.

7. The hemorrhoidecomy apparatus according to claim 6 and wherein said dilator comprises a generally elongate cylindrical body with a generally rounded distal end disposed through said body.

8. The hemorrhoidecomy apparatus according to claim 1 and comprising illumination apparatus disposed through said body.

9. The hemorrhoidecomy apparatus according to claim 1 and comprising illumination apparatus integrated in the anoscope.

* * * * *